United States Patent
Moutafis et al.

(10) Patent No.: US 8,851,866 B2
(45) Date of Patent: Oct. 7, 2014

(54) METHODS AND APPARATUSES FOR JOINING A PUMPING CARTRIDGE TO A PUMP DRIVE

(75) Inventors: Timothy E. Moutafis, Gloucester, MA (US); Edward Bromander, Tewksbury, MA (US)

(73) Assignee: HydroCision, Inc., North Billerica, MA (US)

( * ) Notice: Subject to any disclaimer, the term of this patent is extended or adjusted under 35 U.S.C. 154(b) by 853 days.

(21) Appl. No.: 12/074,294

(22) Filed: Mar. 3, 2008

(65) Prior Publication Data

US 2008/0195058 A1 Aug. 14, 2008

Related U.S. Application Data

(63) Continuation of application No. 10/756,801, filed on Jan. 13, 2004, now Pat. No. 7,337,538, and a continuation-in-part of application No. 10/754,905, filed on Jan. 9, 2004, now Pat. No. 7,717,685, which is a continuation of application No. 10/134,970, filed on Apr. 29, 2002, now abandoned.

(60) Provisional application No. 60/440,123, filed on Jan. 15, 2003, provisional application No. 60/287,219, filed on Apr. 27, 2001.

(51) Int. Cl.
| | |
|---|---|
| F04B 39/10 | (2006.01) |
| F04B 53/12 | (2006.01) |
| F04B 35/01 | (2006.01) |
| F04B 49/00 | (2006.01) |
| F04B 35/00 | (2006.01) |
| A61M 5/315 | (2006.01) |
| F01B 29/00 | (2006.01) |

(52) U.S. Cl.
USPC ........... 417/547; 417/360; 417/214; 417/319; 604/228; 92/128

(58) Field of Classification Search
USPC ........ 417/360, 415, 459, 259, 260, 495, 547, 417/214, 319; 604/228; 92/128
See application file for complete search history.

(56) References Cited

U.S. PATENT DOCUMENTS

| | | | |
|---|---|---|---|
| 1,773,629 A | 8/1930 | Millmine | |
| 2,648,288 A | 8/1953 | Marks | |

(Continued)

FOREIGN PATENT DOCUMENTS

| | | | |
|---|---|---|---|
| DE | 3320076 A1 | 12/1984 | |
| DE | 225618 A1 | 8/1985 | |

(Continued)

OTHER PUBLICATIONS

Baer et al., "Jet-cutting—an alternative to the ultrasonic aspirator?" Chirurg, 61:735, 1990 and Reply to commentary.

(Continued)

*Primary Examiner* — Charles Freay
*Assistant Examiner* — Alexander Comley
(74) *Attorney, Agent, or Firm* — McCarter & English, LLP

(57) ABSTRACT

Embodiments are described for engaging a pumping cartridge with a pump drive. In certain embodiments, the cartridge, including a cylinder and a movable piston assembly, is initially assembled or subsequently positioned so that the distance between the attachment point on the piston assembly for coupling to a drive assembly, and a reference point on the cylinder, is greater than the maximal distance that will be encountered during normal oscillation of the piston during use. The cartridge, in certain embodiments, may be pressed into a drive assembly that immobilizes the cartridge and couples the piston assembly to the driveshaft. In certain embodiments, when the cartridge is fully inserted into the drive assembly, the piston is pressed into the cylinder sufficiently to establish a selected distance so that the piston shaft is in the proper position to engage with a coupling mechanism carried on the driveshaft.

18 Claims, 3 Drawing Sheets

(56) References Cited

U.S. PATENT DOCUMENTS

| | | | |
|---|---|---|---|
| 2,702,547 A * | 2/1955 | Glass | 604/155 |
| RE24,329 E | 6/1957 | Booth | |
| 2,808,302 A | 10/1957 | Bowerman | |
| 2,885,227 A | 5/1959 | Burger | |
| 3,310,283 A | 3/1967 | Carlton | |
| 3,456,915 A | 7/1969 | Smolen | |
| 3,496,874 A | 2/1970 | Findlay | |
| 3,583,710 A | 6/1971 | Burelle | |
| 3,584,982 A * | 6/1971 | Siegel | 417/464 |
| 3,590,813 A | 7/1971 | Roszyk | |
| 3,620,266 A * | 11/1971 | Ryder | 141/20 |
| 3,620,653 A | 11/1971 | Gaylord et al. | |
| 3,719,437 A * | 3/1973 | Schuhmann et al. | 417/360 |
| 3,771,907 A | 11/1973 | Neumann et al. | |
| 3,818,913 A | 6/1974 | Wallach | |
| 3,874,826 A | 4/1975 | Lundquist | |
| 3,930,505 A | 1/1976 | Wallach | |
| 3,994,208 A | 11/1976 | Boyer et al. | |
| 4,009,645 A | 3/1977 | Freimuth | |
| 4,111,490 A | 9/1978 | Liesveld | |
| 4,116,452 A | 9/1978 | Schanz et al. | |
| 4,116,952 A | 9/1978 | Beffa et al. | |
| 4,118,152 A * | 10/1978 | Bron | 417/254 |
| 4,137,804 A | 2/1979 | Gerber et al. | |
| 4,142,524 A | 3/1979 | Jassawalla et al. | |
| 4,155,559 A | 5/1979 | Sieghartner | |
| 4,165,084 A | 8/1979 | Kempf | |
| 4,196,909 A | 4/1980 | Porsch et al. | |
| 4,199,307 A | 4/1980 | Jassawalla | |
| 4,214,507 A | 7/1980 | Hock et al. | |
| 4,216,906 A | 8/1980 | Olsen et al. | |
| 4,267,862 A | 5/1981 | Neff et al. | |
| 4,270,440 A | 6/1981 | Lewis, II | |
| 4,270,990 A | 6/1981 | Fong | |
| 4,281,590 A | 8/1981 | Weaver | |
| 4,303,376 A * | 12/1981 | Siekmann | 417/360 |
| 4,304,531 A | 12/1981 | Fisher et al. | |
| 4,336,800 A | 6/1982 | Pastrone | |
| 4,336,946 A | 6/1982 | Wheeler | |
| 4,410,322 A | 10/1983 | Archibald | |
| 4,435,902 A | 3/1984 | Mercer et al. | |
| 4,465,438 A | 8/1984 | Brauer et al. | |
| 4,479,760 A | 10/1984 | Bilstad et al. | |
| 4,479,761 A | 10/1984 | Bilstad | |
| 4,479,762 A | 10/1984 | Bilstad et al. | |
| 4,517,977 A | 5/1985 | Frost et al. | |
| 4,521,027 A | 6/1985 | Marshall | |
| 4,557,725 A | 12/1985 | Heyne et al. | |
| 4,560,373 A | 12/1985 | Sugino et al. | |
| 4,573,883 A | 3/1986 | Noon et al. | |
| 4,601,235 A | 7/1986 | Roberts | |
| 4,614,481 A | 9/1986 | Vanderjagt | |
| 4,632,669 A * | 12/1986 | Phipps et al. | 604/118 |
| 4,635,621 A | 1/1987 | Atkinson | |
| 4,637,551 A | 1/1987 | Seeger, Jr. et al. | |
| 4,657,490 A | 4/1987 | Abbott | |
| 4,662,829 A | 5/1987 | Nehring | |
| 4,677,980 A * | 7/1987 | Reilly et al. | 600/432 |
| 4,690,672 A | 9/1987 | Veltrup et al. | |
| 4,730,550 A | 3/1988 | Bramstedt et al. | |
| 4,735,129 A | 4/1988 | Sjoberg | |
| 4,741,678 A | 5/1988 | Nehring | |
| 4,743,033 A | 5/1988 | Guess | |
| 4,749,337 A | 6/1988 | Dickinson et al. | |
| 4,754,929 A | 7/1988 | Struve et al. | |
| 4,761,039 A | 8/1988 | Hilaris | |
| 4,776,616 A | 10/1988 | Umehara et al. | |
| 4,776,769 A | 10/1988 | Hilaris | |
| 4,795,217 A | 1/1989 | Hilaris | |
| 4,798,339 A | 1/1989 | Sugino et al. | |
| 4,798,589 A | 1/1989 | Tseo | |
| 4,811,902 A | 3/1989 | Nagata et al. | |
| 4,813,343 A | 3/1989 | Schaefer | |
| 4,818,190 A | 4/1989 | Pelmulder et al. | |
| 4,827,679 A | 5/1989 | Earle, III | |
| 4,832,581 A * | 5/1989 | Muller et al. | 417/383 |
| 4,842,584 A | 6/1989 | Pastrone | |
| 4,857,048 A | 8/1989 | Simons et al. | |
| 4,872,813 A | 10/1989 | Gorton et al. | |
| 4,896,085 A | 1/1990 | Jones | |
| 4,898,574 A | 2/1990 | Uchiyama et al. | |
| 4,898,579 A | 2/1990 | Groshong et al. | |
| 4,913,698 A | 4/1990 | Ito et al. | |
| 4,921,409 A | 5/1990 | Besic | |
| 4,922,900 A * | 5/1990 | Kiske et al. | 128/202.27 |
| 4,927,411 A | 5/1990 | Pastrone et al. | |
| 4,932,114 A | 6/1990 | Morse et al. | |
| 4,937,985 A | 7/1990 | Boers et al. | |
| 4,940,399 A | 7/1990 | Gorton et al. | |
| 4,950,238 A | 8/1990 | Sullivan | |
| 4,958,963 A | 9/1990 | Perrault et al. | |
| 4,973,308 A * | 11/1990 | Borras et al. | 604/110 |
| 5,002,316 A | 3/1991 | Chohan | |
| 5,006,043 A | 4/1991 | Katsumata et al. | |
| 5,006,050 A | 4/1991 | Cooke et al. | |
| 5,011,468 A | 4/1991 | Lundquist et al. | |
| 5,018,670 A | 5/1991 | Chalmers | |
| 5,027,792 A | 7/1991 | Meyer | |
| 5,037,431 A | 8/1991 | Summers et al. | |
| 5,052,624 A | 10/1991 | Boers et al. | |
| 5,056,992 A | 10/1991 | Simons et al. | |
| 5,074,862 A | 12/1991 | Rausis et al. | |
| 5,087,056 A | 2/1992 | Baglin et al. | |
| 5,092,744 A | 3/1992 | Boers et al. | |
| 5,098,262 A | 3/1992 | Wecker et al. | |
| 5,111,652 A | 5/1992 | Andre et al. | |
| 5,125,582 A | 6/1992 | Surjaatmadja et al. | |
| 5,133,687 A | 7/1992 | Malloy | |
| 5,135,482 A | 8/1992 | Neracher et al. | |
| 5,154,589 A | 10/1992 | Ruhl et al. | |
| 5,162,016 A | 11/1992 | Malloy | |
| 5,171,045 A | 12/1992 | Pasbrig et al. | |
| 5,186,615 A | 2/1993 | Karliner | |
| 5,195,754 A | 3/1993 | Dietle | |
| 5,197,955 A | 3/1993 | Stephens et al. | |
| 5,201,643 A | 4/1993 | Hirosawa et al. | |
| 5,205,779 A | 4/1993 | O'Brien et al. | |
| 5,211,633 A | 5/1993 | Stouder, Jr. | |
| 5,217,465 A | 6/1993 | Steppe | |
| 5,230,443 A | 7/1993 | Du | |
| 5,237,309 A | 8/1993 | Frantz et al. | |
| 5,250,065 A | 10/1993 | Clement et al. | |
| 5,259,842 A | 11/1993 | Plechinger et al. | |
| 5,261,883 A | 11/1993 | Hood et al. | |
| 5,281,108 A | 1/1994 | Brooke | |
| 5,284,084 A | 2/1994 | Pippert et al. | |
| 5,290,245 A | 3/1994 | Dennis | |
| 5,314,375 A | 5/1994 | O'Brien et al. | |
| 5,322,504 A | 6/1994 | Doherty et al. | |
| 5,336,201 A * | 8/1994 | von der Decken | 604/223 |
| 5,339,715 A | 8/1994 | Coleman et al. | |
| 5,344,292 A | 9/1994 | Rabenau et al. | |
| 5,364,234 A | 11/1994 | Eickmann | |
| 5,368,452 A | 11/1994 | Johnson et al. | |
| 5,370,609 A | 12/1994 | Drasler et al. | |
| 5,378,126 A | 1/1995 | Abrahamson et al. | |
| 5,392,694 A | 2/1995 | Muller et al. | |
| 5,411,380 A | 5/1995 | Bristol et al. | |
| 5,415,528 A | 5/1995 | Ogden et al. | |
| 5,429,485 A | 7/1995 | Dodge | |
| 5,449,369 A | 9/1995 | Imran | |
| 5,464,392 A | 11/1995 | Epstein et al. | |
| 5,476,368 A | 12/1995 | Rabenau et al. | |
| 5,480,163 A | 1/1996 | Miser et al. | |
| 5,482,297 A | 1/1996 | Burns et al. | |
| 5,490,680 A | 2/1996 | Patel et al. | |
| 5,494,410 A * | 2/1996 | Maier-Laxhuber et al. | 417/53 |
| 5,496,267 A | 3/1996 | Drasler et al. | |
| 5,505,729 A | 4/1996 | Rau et al. | |
| 5,509,911 A | 4/1996 | Cottone, Sr. et al. | |
| 5,511,464 A | 4/1996 | Cezanne et al. | |
| 5,533,879 A | 7/1996 | Chen et al. | |
| 5,540,568 A | 7/1996 | Rosen et al. | |
| 5,542,918 A | 8/1996 | Atkinson | |

(56) References Cited

U.S. PATENT DOCUMENTS

| | | | |
|---|---|---|---|
| 5,554,013 A | 9/1996 | Owens et al. | |
| 5,558,646 A | 9/1996 | Roche | |
| 5,562,186 A | 10/1996 | Osenbaugh | |
| 5,562,692 A | 10/1996 | Bair | |
| 5,568,868 A | 10/1996 | Keller et al. | |
| 5,577,896 A * | 11/1996 | Harada | 417/259 |
| 5,591,184 A | 1/1997 | McDonnell et al. | |
| 5,607,391 A | 3/1997 | Klinger et al. | |
| 5,620,414 A * | 4/1997 | Campbell, Jr. | 604/22 |
| 5,626,072 A | 5/1997 | Mirand et al. | |
| 5,632,606 A | 5/1997 | Jacobsen et al. | |
| 5,647,852 A | 7/1997 | Atkinson | |
| 5,667,102 A | 9/1997 | Keller et al. | |
| 5,674,226 A | 10/1997 | Doherty et al. | |
| 5,711,151 A | 1/1998 | Engfer | |
| 5,713,878 A * | 2/1998 | Moutafis et al. | 604/534 |
| 5,735,815 A | 4/1998 | Bair | |
| 5,749,885 A | 5/1998 | Sjostrom et al. | |
| 5,842,701 A | 12/1998 | Cawthorne et al. | |
| 5,845,749 A | 12/1998 | Moretz et al. | |
| 5,849,023 A | 12/1998 | Mericle | |
| 5,865,442 A | 2/1999 | Iwashita et al. | |
| 5,865,992 A | 2/1999 | Edmondson | |
| 5,871,462 A | 2/1999 | Yoder et al. | |
| 5,899,915 A | 5/1999 | Saadat | |
| 5,941,162 A | 8/1999 | Kiesel | |
| 5,944,686 A * | 8/1999 | Patterson et al. | 604/22 |
| 5,960,700 A | 10/1999 | Staggs et al. | |
| 6,017,354 A | 1/2000 | Culp et al. | |
| 6,027,502 A | 2/2000 | Desai | |
| 6,042,571 A * | 3/2000 | Hjertman et al. | 604/208 |
| 6,045,564 A | 4/2000 | Walen | |
| 6,066,150 A | 5/2000 | Gonon et al. | |
| 6,079,313 A * | 6/2000 | Wolcott et al. | 92/71 |
| 6,083,189 A | 7/2000 | Gonon et al. | |
| 6,085,631 A | 7/2000 | Kownacki | |
| 6,096,001 A | 8/2000 | Drasler et al. | |
| 6,142,484 A | 11/2000 | Valls, Jr. | |
| 6,155,806 A * | 12/2000 | Andel | 417/523 |
| 6,161,834 A | 12/2000 | Pollack et al. | |
| 6,216,573 B1 | 4/2001 | Moutafis et al. | |
| 6,280,302 B1 | 8/2001 | Hashish et al. | |
| 6,322,533 B1 | 11/2001 | Gonon et al. | |
| 6,375,635 B1 | 4/2002 | Moutafis et al. | |
| 6,378,737 B1 | 4/2002 | Cavallaro et al. | |
| 6,402,715 B2 | 6/2002 | Manhes et al. | |
| 6,419,654 B1 | 7/2002 | Kadan | |
| 6,423,028 B1 | 7/2002 | Gonon et al. | |
| 6,451,017 B1 | 9/2002 | Moutafis et al. | |
| 6,464,567 B2 | 10/2002 | Hashish et al. | |
| 6,491,660 B2 | 12/2002 | Guo et al. | |
| 6,508,823 B1 | 1/2003 | Gonon et al. | |
| 6,511,493 B1 | 1/2003 | Moutafis et al. | |
| 6,544,220 B2 | 4/2003 | Shuman et al. | |
| 6,669,710 B2 | 12/2003 | Moutafis et al. | |
| 6,899,712 B2 | 5/2005 | Moutafis et al. | |
| 6,923,792 B2 | 8/2005 | Staid et al. | |
| 6,960,182 B2 | 11/2005 | Moutafis et al. | |
| 7,293,967 B2 * | 11/2007 | Fukano et al. | 417/413.1 |
| 7,337,538 B2 | 3/2008 | Moutafis et al. | |
| 7,717,685 B2 | 5/2010 | Moutafis et al. | |
| 2001/0002562 A1 | 6/2001 | Moutafis et al. | |
| 2002/0022807 A1* | 2/2002 | Duchon et al. | 604/228 |
| 2002/0050197 A1 | 5/2002 | Moutafis et al. | |
| 2002/0169421 A1* | 11/2002 | McWethy et al. | 604/192 |
| 2002/0176788 A1* | 11/2002 | Moutafis et al. | 417/415 |
| 2002/0177802 A1 | 11/2002 | Moutafis et al. | |
| 2003/0009166 A1 | 1/2003 | Moutafis et al. | |
| 2003/0040763 A1 | 2/2003 | Moutafis et al. | |
| 2003/0055404 A1 | 3/2003 | Moutafis | |
| 2003/0083681 A1 | 5/2003 | Moutafis et al. | |
| 2003/0125660 A1 | 7/2003 | Moutafis et al. | |
| 2004/0228736 A1 | 11/2004 | Moutafis et al. | |
| 2004/0230211 A1 | 11/2004 | Moutafis et al. | |
| 2004/0234380 A1 | 11/2004 | Moutafis et al. | |
| 2004/0243157 A1 | 12/2004 | Connor et al. | |

FOREIGN PATENT DOCUMENTS

| | | |
|---|---|---|
| DE | 3421390 A1 | 12/1985 |
| DE | 4201992 A1 | 11/1993 |
| DE | 19734890 C1 | 7/1999 |
| EP | 0411170 A1 | 2/1991 |
| EP | 0420781 A2 | 4/1991 |
| EP | 0482133 A1 | 5/1992 |
| EP | 0489496 A1 | 6/1992 |
| EP | 0551920 A1 | 7/1993 |
| EP | 0555549 A1 | 8/1993 |
| EP | 0636345 A1 | 2/1995 |
| EP | 0855507 A2 | 7/1998 |
| FR | 1241277 A | 9/1960 |
| FR | 2094507 A | 2/1972 |
| GB | 199057 A | 6/1923 |
| GB | 651836 A | 4/1951 |
| WO | WO-94/14584 A1 | 7/1994 |
| WO | WO-96/40476 A1 | 12/1996 |
| WO | WO-99/33510 A1 | 7/1999 |
| WO | WO-02/095234 A1 | 11/2002 |
| WO | WO-03/013645 A1 | 2/2003 |
| WO | WO-03/024340 A2 | 3/2003 |

OTHER PUBLICATIONS

Baer et al., "New water-jet dissector: initial experience in hepatic surgery," Br. J. Surg., vol. 78, pp. 502-503, Apr. 1991.

Baer et al., "Water-jet dissection in hepatic surgery," Minimally Invasive Therapy, vol. 1, pp. 169-172, 1992.

Baer et al., "Hepatic Surgery Facilitated by a New Jet Dissector," HPB Surgery, vol. 4, pp. 137-146, 1991.

Drasler et al., "A rheolytic system for percutaneous coronary and peripheral plaque removal," Angiology—The Journal of Vascular Diseases, Feb. 1991, vol. 42, No. 2, pp. 90-98.

Drasler et al., "Rheolytic catheter for percutaneous removal of thrombus," Radiology, Jan. 1992, vol. 182, pp. 263-267.

Field, J.E. et al., "The physics of liquid impact, shock wave interactions with cavities, and the implications to shock wave lithotripsy," Phys. Med. Biol., vol. 36, No. 11, pp. 1475-1484, 1991.

Giraud et al., "Bone cutting," Clin. Phys. Physiol. Meas., vol. 12, No. 1, pp. 1-19, 1991.

Izumi et al., "Hepatic resection using a water jet dissector," Surgery Today Jpn. J. Surg., vol. 23, pp. 31-35, 1993.

Papachristou et al., "Resection of the liver with a water jet," Br. J. Surg., 1982, vol. 69, pp. 93-94.

Terzis et al., "A new system for cutting brain tissue preserving vessels: water jet cutting," British Journal of Neurosurgery, vol. 3, pp. 361-366, 1989.

Zhong et al., "Propagation of shock waves in elastic solids caused by cavitation microjet impact. II: Application in extracorporeal shock wave lithotripsy," J. Acoust. Soc. Am., vol. 94, No. 1, pp. 29-36, Jul. 1993.

Water Jet Dissector, Hepatotom□ Supersonic Microjet Dissector brochure, Medical Exports AG.

Official Communication from corresponding Canadian Patent Application No. 2,484,061, dated Aug. 19, 2005.

Official Communication from corresponding Canadian Patent Application No. 2,484,061, dated Apr. 10, 2006.

Official Communication from corresponding European Patent Application No. 02729070.9, dated Sep. 16, 2004.

(56) References Cited

OTHER PUBLICATIONS

Official Communication from corresponding European Patent Application No. 02729070.9, dated Feb. 14, 2006 and Claims as Pending.
Tikhomirov, R.A. et al., "High-Pressure Jet Cutting TJ840 G5313," 1992.
International Search Report Oct. 8, 2001 of U.S. PCT 2001/00785.
International Search Report Nov. 4, 2002 of U.S. PCT 2002/13608.
International Search Report Dec. 10, 2002 of U.S. PCT 2002/25133.
Communication Pursuant to Article 96(2) EPC, dated Aug. 29, 2005 for corresponding European patent application serial No. 02768451.3-2310.
Communication for corresponding Canadian patent application serial No. 2,493,238, dated Jun. 15, 2005.
Communication for corresponding Australian patent application serial No. 2002331012, dated Feb. 14, 2005.
Office Action dated Jan. 27, 2004 from U.S. Appl. No. 10/032,385.

* cited by examiner

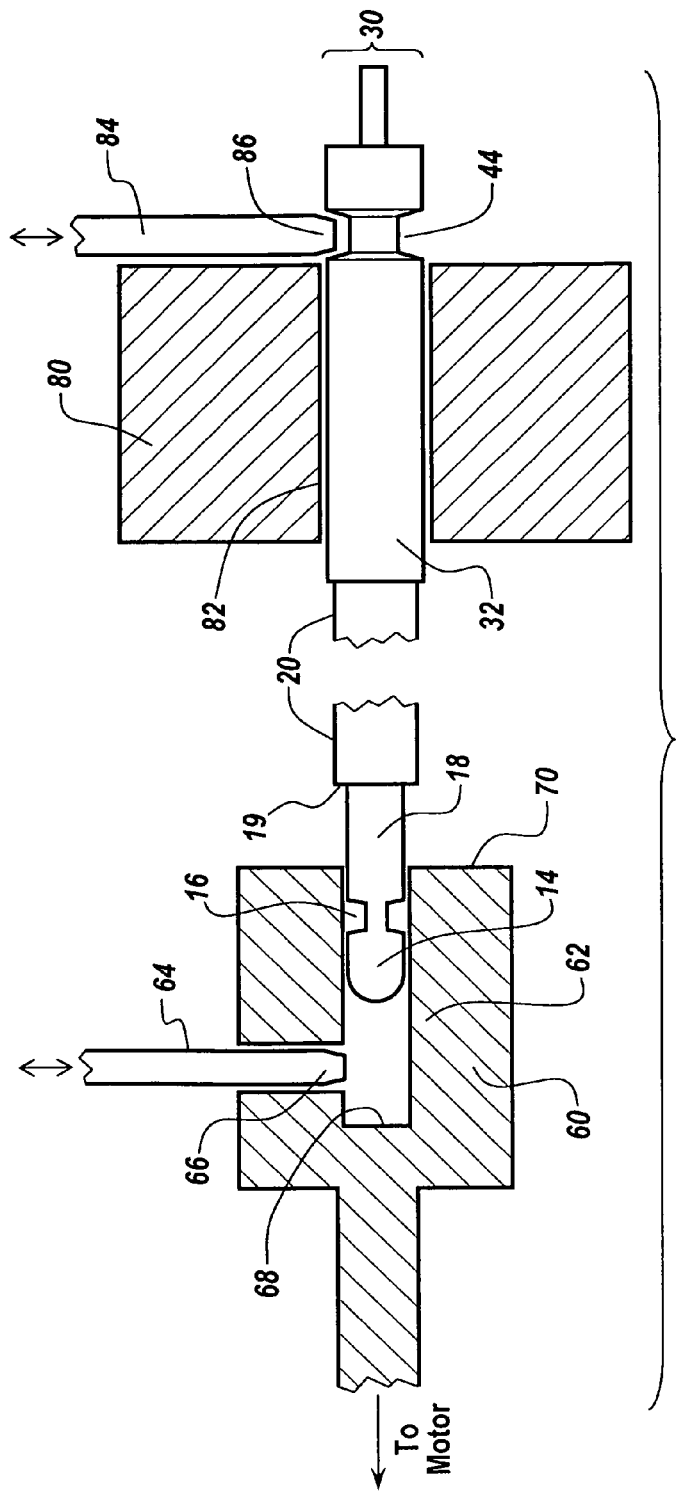
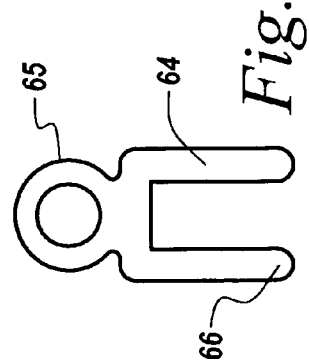
Fig. 2
Fig. 2A

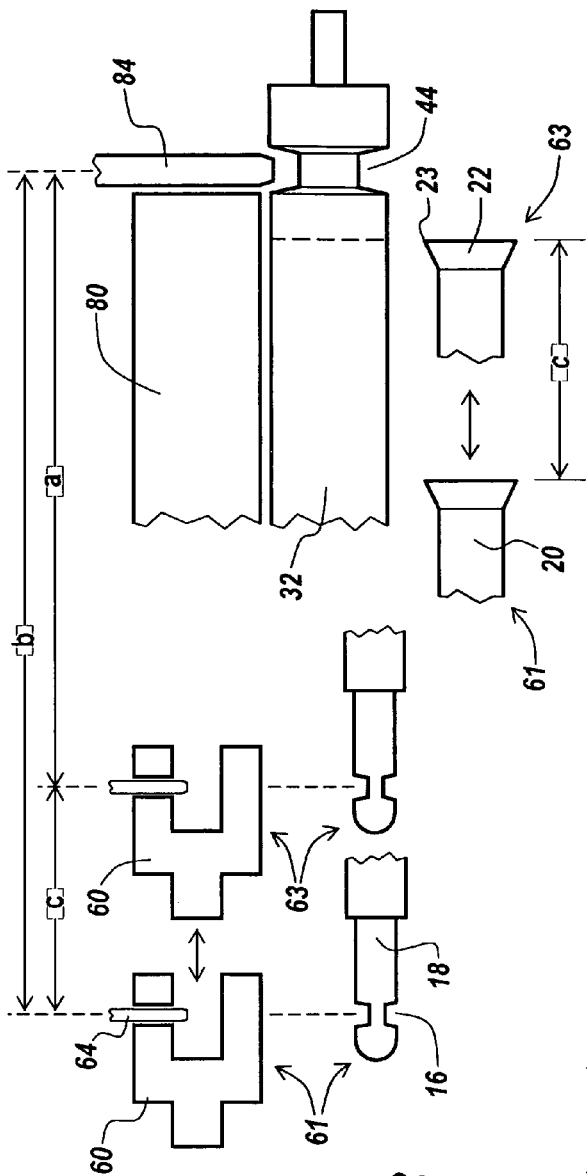
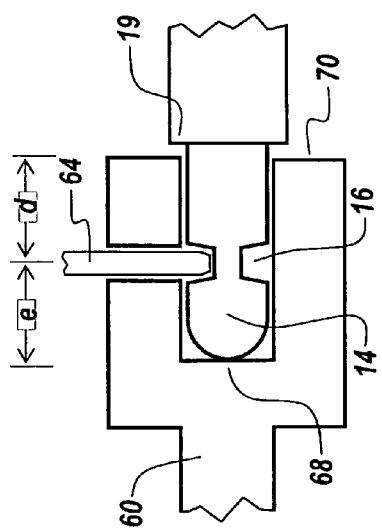
Fig. 3
Fig. 4

METHODS AND APPARATUSES FOR JOINING A PUMPING CARTRIDGE TO A PUMP DRIVE

Related Applications

This application is a continuation of U.S. patent application Ser. No. 10/756,801, filed Jan. 13, 2004, which claims the benefit of U.S. Provisional Patent Application Ser. No. 60/440,123 filed Jan. 15, 2003. This application is a continuation-in-part of U.S. patent application Ser. No. 10/754,905 filed Jan. 9, 2004 which is a continuation of U.S. patent application Ser. No. 10/134,970, filed Apr. 29, 2002, now abandoned, which claims priority to U.S. Provisional Patent Application Ser. No. 60/287,219, filed Apr. 27, 2001. The content of each of the foregoing U.S. patent applications is herein incorporated by reference.

BACKGROUND

1. Field of the Invention

The invention relates generally to pumping systems employing pumping cartridges that can be disengaged from a pump drive unit, and, more specifically to methods of joining a pumping cartridge to a pump drive in such pumping systems and interconnect mechanisms facilitating such methods.

2. Description of the Related Art

A piston pump typically includes several cooperating elements. These typically include at least a cylinder, a piston moving in the cylinder, and a drive shaft connected to the piston that moves the piston back and forth in the cylinder. Other elements typically include one or more check valves, or functional equivalents, so that fluid is drawn in from a source and expelled into an outlet. Normally, the drive shaft is permanently fastened to a mechanism providing the reciprocal motion.

In certain medical applications, it may be desirable to provide disposable pump elements that contact fluids being pumped, e.g. disposable piston pumping cartridges, for example to prevent transmission of disease between patients. For the sake of economy, it may be advantageous for the mechanism providing reciprocating force to be separate from the pumping elements. The disposable portion of a piston pump, typically comprising a cylinder, a piston, and valves, can advantageously be fabricated as a separate cartridge. The cartridge can, for certain applications, be provided in a sterile condition, so that the fluid pumped will not be contaminated. Such a cartridge can be configured to be reversibly attached to a reusable drive mechanism, typically comprising a motor, which reciprocates the piston via, for example, a reversible linkage.

In one mode of medical use, such as described in certain of the Applicant's commonly owned patents and patent applications (e.g. U.S. Pat. Nos. 6,216,573; 5,944,686; 6,375,635; 6,511,493; and U.S. Pat. Application Pub. No. 2002/0176788-A1, each incorporated herein by reference), such a disposable cartridge can used to generate a high pressure, such as 5,000 p.s.i, 10,000 p.s.i, or 20,000 p.s.i or more. The resulting high pressure water jet can be used, for example, to cut and/or remove and/or clean tissue, or to drive rotary tissue-abrading elements. In one mode of making such cartridges, described in more detail in commonly-owned US 2002/0176788-A1, the piston is provided with an abradable flange as a sealing element. Such disposable cartridges may, in certain embodiments, be designed to be used only for a single medical procedure, and thus may require relatively frequent replacement.

In a medical environment, such as an operating room, there are several constraints that may be desirable to be satisfied in a procedure for coupling a piston to a drive that make such a procedure technically challenging. First, it may be desirable that the connection can be made without removing the piston from the cylinder, since that would tend to render the pumping zone non-sterile. Second, may be desirable for it to be possible for the operator to be able to replace the pump while the operator is wearing gloves, and without contaminating the operator (who will typically be a physician or a nurse.) Third, it may be desirable that the connection method can enable the disposable components to be coupled to the reusable components reliably on the first try and without extensive operator training or difficulty. In addition, it may be desirable that the connection mechanism be able to be fabricated economically so as to add as little expense to the overall disposable cartridge as possible.

SUMMARY

Apparatuses and methods for connecting a disposable pumping cartridge to a pump drive that can, in certain embodiments, meet one, more, or all of the above requirements are described. In an exemplary embodiment, a method and system of coupling is described that comprises "parking" a piston in a portion of a cylinder that is other than its normal operating zone, and that is positioned farther from a high pressure fluid-containing end of the cartridge than the operating zone. This "Parking" procedure can be used to position a piston in a cylinder so than when the cartridge is inserted into a drive, the piston can, optionally without further intervention, be positioned so that a provided coupling mechanism can, in some cases reliably and simply, couple the piston to the drive mechanism.

Apparatus and methods of their use are described for engaging a pumping cartridge with a pump drive. In certain embodiments, the cartridge, comprising a cylinder and a movable piston assembly, is initially assembled or subsequently positioned so that the distance between the attachment point on the piston assembly for coupling to a drive assembly, and a reference point on the cylinder, is greater than the maximal distance that will be encountered during normal oscillation of the piston during use. The cartridge, in certain embodiments may be pressed into a drive assembly having means for immobilizing the cartridge and means for coupling the piston assembly to the driveshaft. In certain embodiments, when the cartridge is fully inserted into the drive assembly, the piston is pressed into the cylinder sufficiently to establish a selected distance so that the piston shaft is in the proper position to engage with a coupling mechanism carried on the driveshaft.

In a first series of embodiments, a method for reversibly coupling a pumping cartridge to a reusable pump drive system is described. The method comprises: providing the reusable pump drive system with a first pumping cartridge retaining component configured and positioned to enable it to engage a first portion of the cartridge, the first pumping cartridge retaining component being adjustable between a retaining position and a non-retaining position; providing a driveshaft of the reusable pump drive system with a second pumping cartridge retaining component configured and positioned to enable it to engage a second portion of the cartridge comprising a portion of a piston shaft of the pumping cartridge, the second pumping cartridge retaining component being adjustable between a retaining position and a non-retaining position; preparing the pumping cartridge for connection to the reusable pump drive system by placing a piston of the pumping cartridge in a selected position relative to a cylinder of the pumping cartridge; inserting the pumping cartridge into the reusable pump drive system; adjusting the first and second pumping cartridge retaining components to their non-retaining positions; and moving at least one of the first and second pumping cartridge retaining components to its retaining position.

In certain such embodiments, the selected position is chosen so that the first portion of the cartridge and the second portion of the cartridge are separated by a distance enabling both the first and second pumping cartridge retaining components to be positioned in their retaining positions. The selected position can then be obtained by the steps of: moving the piston relative to the cylinder so that a distance separating the first portion of the pumping cartridge and the second portion of the pumping cartridge comprising a portion of the piston shaft is greater that an engaging distance separating the first portion of the pumping cartridge and the second portion of the pumping cartridge comprising a portion of the piston shaft; and inserting the pumping cartridge into the pump drive system so that during insertion of the cartridge into the pump drive system the piston is moved into the selected position, wherein the distance separating the first portion of the pumping cartridge and the second portion of the pumping cartridge comprises the engaging distance.

In certain embodiments of the first series of embodiments, the selected position is indicated by a detectable position indicator, while in these or other embodiments, after the moving step, a step of using the pumping cartridge in a medical pumping procedure is performed. In certain of these or other embodiments, the pumping cartridge is constructed and arranged to enable it to withstand and generates a pressure of at least about 5,000 p.s.i., without failure or leakage.

In certain embodiments of the first series of embodiments, the selected distance is obtained by engaging the first portion of the pumping cartridge with the first pumping cartridge retaining component; moving the driveshaft of the pump drive system to a first end of its range, wherein the driveshaft is in its distal-most position in which a distance between a distal end of the driveshaft and the cylinder is as small as possible; and then engaging the second pumping cartridge retaining component with the second portion of the pumping cartridge comprising the portion of the piston shaft.

In another series of embodiments, a method for reversibly coupling a pumping cartridge to a driveshaft of a reusable pump drive system is disclosed. The method comprises: providing the reusable pump drive system with a first pumping cartridge retaining component configured and positioned to enable it to engage a first portion of the cartridge, the first pumping cartridge retaining component being adjustable between a retaining position and a non-retaining position; providing a driveshaft of the reusable pump drive system with a second pumping cartridge retaining component configured and positioned to enable it to engage a second portion of the cartridge comprising a portion of a piston shaft of the pumping cartridge, the second pumping cartridge retaining component being adjustable between a retaining position and a non-retaining position; inserting the pumping cartridge into the pump drive system; adjusting the first pumping cartridge retaining component to the retaining position; moving the driveshaft of the pump drive system to a first end of its range, wherein the driveshaft is in its distal-most position in which a distance between a distal end of the driveshaft and the cylinder is as small as possible; and engaging said second pumping cartridge retaining component with the second portion of the cartridge comprising a portion of the piston shaft of the pumping cartridge, so as to couple the piston shaft to the driveshaft.

In yet another series of embodiments, a method for coupling a presterilized pumping cartridge to a reusable pump drive assembly is disclosed. The method comprises: positioning a piston assembly portion of the pumping cartridge in a first position within the cylinder, the first position being proximal to an operating region of the cylinder in which a piston reciprocates during operation; sterilizing at least a cylinder assembly portion of the pumping cartridge; inserting the cartridge sterilized in the sterilizing step into the pump drive assembly; engaging a first retaining component of the pump drive assembly with a first portion of the cartridge; and engaging a second retaining component of a driveshaft of the pump drive assembly with the piston assembly portion of the cartridge. In certain embodiments of the method, before sterilizing the cartridge, a step of sealing the pumping cartridge in sterilizable packaging can be performed. In certain of these or other embodiments, the cartridge may be removed from the sterilizable packaging after sterilization.

BRIEF DESCRIPTION OF THE DRAWINGS

The accompanying drawings are schematic are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention. In the drawings:

FIG. 2 is a schematic cross-sectional illustration of portions of a cartridge inserted into an adaptor on a drive shaft that connects to a pump drive (not illustrated), according to one embodiment of the invention;

FIG. 2A is a schematic illustration of one embodiment of a piston shaft engaging member of the pump drive shaft of FIG. 2;

FIG. 3 is a schematic cross-sectional illustration of portions of a pumping cartridge assembly and an adaptor on a drive shaft that connects to a pump drive (not illustrated) illustrating certain dimensional and positional relationships among the components, according to certain embodiments of the invention; and FIG. 4 is a schematic cross-sectional illustration of portions of a pumping cartridge assembly and an adaptor on a drive shaft that connects to a pump drive (not illustrated) illustrating certain dimensional and positional relationships among the components, according to certain embodiments of the invention.

DETAILED DESCRIPTION

Figure 1:
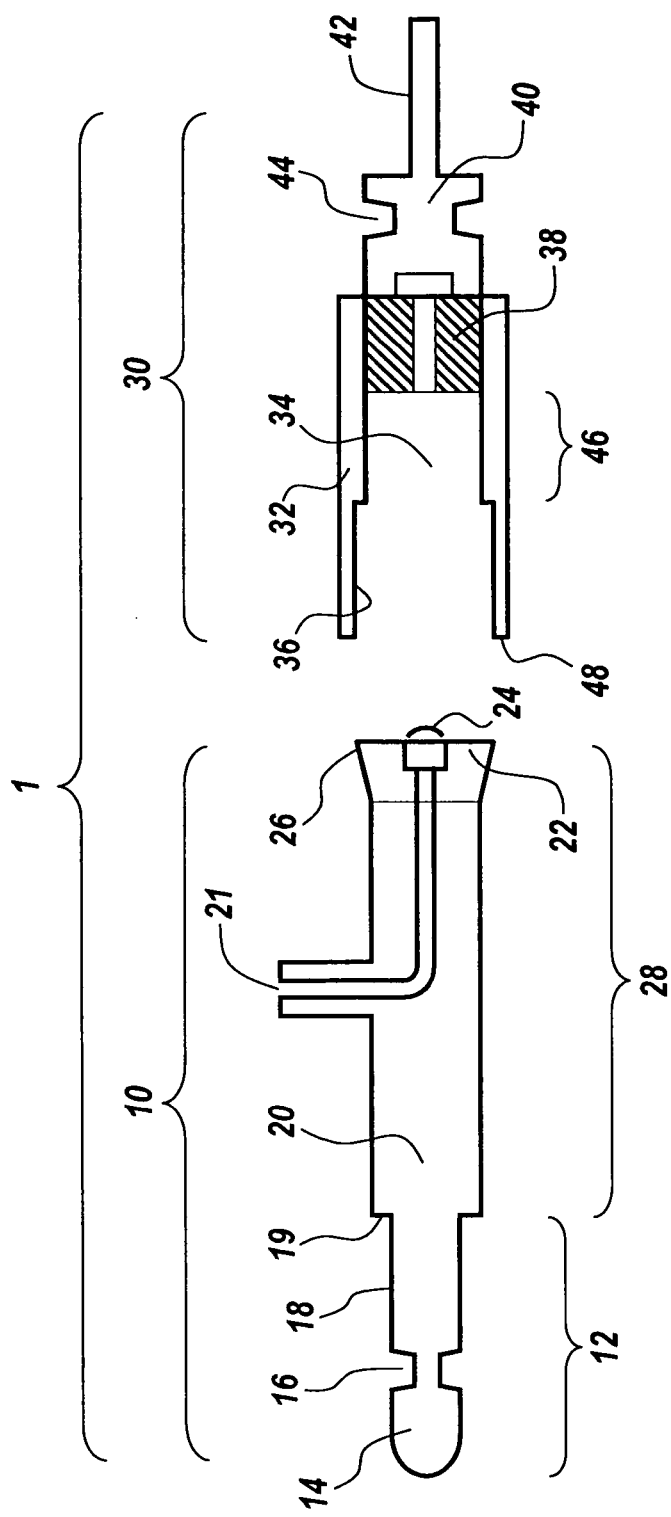
FIG. 1 is a schematic cross-sectional illustration of portions of a pumping cartridge assembly according to one embodiment of the invention.

To more clearly illustrate certain aspects of the invention, a particular, exemplary embodiment is described below. Numerous variations are possible that encompass the same invention, and the invention is limited only by the claims appended hereto, and is not limited to the exemplary configurations and dimensions set forth in this detailed description.

FIG. 1 is a schematic illustration showing a pumping cartridge assembly, according to an embodiment of the invention, generally labeled 1. The cartridge, in this embodiment, has two parts, a piston assembly 10 and a cylinder assembly 30. The piston assembly 10 has a connecting region 12 and a body region 28. The connecting region 12 comprises a terminal knob 14, a groove 16, and a shaft 18 meeting body 20 at lip 19. Body region 28 has a body 20, a fluid inlet 21 connecting with a check valve 24 (the structure of which is described in greater detail in US 2002/0176788-A1); and a piston 22 carried on body 20 and having a sealing flange 26 (the structure of which is described in greater detail in US 2002/0176788-A1). The flange 26, in certain embodiments, protrudes slightly beyond the diameter of the body 20 and the piston 22 to provide a seal against the cylinder wall. The flange 26 may be designed to be erodible in use. The check valve 24 may be oriented so that fluid can move into inlet 21 and out of the check valve, but cannot flow back into the check valve when the piston compresses the fluid. In other words, the check calve 24 may be arranged so that fluid flows to the right ("distally") in the cartridge as illustrated.

The other portion of the cartridge of the particular embodiment illustrated is the cylinder assembly 30. The cylinder assembly 30 comprises a wall 32 surrounding a cavity 34. The cavity may be slightly broader at a proximal portion 36 forming a piston storage region to accommodate the flange 26 when the piston is not in use. This "parked" position can prevent or reduce irreversible deformation of the flange 26 during storage, and is also useful for positioning of the piston, as described below. A second check valve is positioned at 38, likewise oriented so that fluid flows only to the right (distally). An outlet fitting 40 carries a barb or other hose connection 42, and a positioning notch 44. In normal operation, the piston reciprocates in a defined zone 46, which is distal of the "parking" zone (i.e. piston storage region) demarcated by relief 36.

Many other detailed constructions of a cartridge are possible; several are illustrated and/or described in US 2002-0176788-A1. As will be seen below, some features of a cartridge that may be advantageous for use in certain embodiments of the invention are the existence of positioning elements on each of the piston assembly and the cylinder that comprise or are functionally equivalent or similar to groove 16 and notch 44. A second feature, provided in some embodiments, is the ability of the piston assembly to remain assembled in the cartridge while outside of (proximal to) its normal operating zone, i.e., to be parked or stored.

FIG. 2 is a schematic illustration of a cartridge inserted into an adaptor 60 on a drive shaft that connects to a pump drive mechanism (not illustrated). The drive mechanism will typically will comprise a motor with appropriate controls, gearing, etc., and will be configured to cause the drive shaft adaptor 60 to reciprocate in the proximal/distal direction. Drive shaft adaptor 60 has a cavity 62, which may be slightly larger in diameter than piston shaft 18, and a back end at 68 and a front end at 70. Drive shaft adaptor 60 also may have one or more piston shaft retaining components, such as one or more movable pins (or functional equivalent) 64. Pins 64 may have a rounded inner end 66 designed to facilitate engagement with and to fit into groove 16 on the piston shaft 18. When pin 64 is lowered and groove 16 is below pin 64 so that the lower end 66 of the pin is in the groove, then the piston assembly 10 is locked to drive shaft adaptor 60 and can reciprocate with it.

When pin 64 is raised, piston shaft 18 can be withdrawn from cavity 62 and removed from the adaptor 60. Apparatus for raising and lowering pins 64 or equivalent is not illustrated, and may take many forms, as would be apparent to those skilled in the art. In one embodiment, FIG. 2A, a pair of pins 64 connected to a ring 65, which can be looped around an elongated raising member (not shown), and slide freely along the raising member when the drive shaft reciprocates. When the driving mechanism is turned off and the raising member is raised, the pins are lifted sufficiently to allow removal or inserting of a piston shaft 18. With such a design, removal is possible at any point in the stroke of the driveshaft. The pins could be replaced with a blade, or prongs, or other devices, and moved to engage the shaft, and removed to disengage the shaft, from any direction, including from below, or from the side, or from more than one direction, as would be apparent to those skilled in the art. Insertion of the pair of pins 64 can be by gravity, but in some embodiments there is a bottom segment to the loop so that the raising member can also push the pins downward so as to engage groove 16 (see FIG. 2A.)

Referring again to FIG. 2, a block 80 has a cylindrical passage 82 through it that may be slightly larger in diameter than cylinder outer wall 32. Associated with block 80 is a pump cartridge cylinder retaining component 84 with an inner end 86 that is sized and positionable to fit into notch 44 of the cylinder assembly. Retainer 84 is shown in a closed configuration in which it retains the cylinder assembly 30 in the passage 82, and retainer 84 may be configured so that it can be raised to release the cartridge, or to allow insertion of the cartridge. The raising mechanism can take any of a variety of forms, as would be apparent to those skilled in the art, and is not illustrated. Optionally, the raising mechanism for retainer 84 may be coupled to the raising mechanism for pin 64, in embodiments which allow the simultaneous operation of the two latching mechanisms.

Driveshaft adaptor 60 operates within a drive assembly (not illustrated) in which the position of block 80 is fixed. (Other components of the drive assembly can typically include the housing and the motor and its controls, which are typically fixed in relation to block 80). The pump drive assembly (which may also be called a console, or similar terms) is typically covered with a housing preventing operator contact with moving parts and electrical or electronic components, etc. Pin 64 may be connected to a lifting and lowering mechanism, which in one embodiment, as described above, is constructed so that pin 64 can reciprocate along with driveshaft adaptor 60, and still be raised when removal of the removable pumping cartridge from the pump drive assembly is desired. Optionally, the pump drive assembly may be constructed, for example by provision of mechanical or electronic interlocks, so that neither pin 64 nor retainer 84 can be raised while driveshaft 60 is in motion.

The exemplary configuration illustrated in FIG. 2 demonstrates one of the problems that could occur when inserting a cartridge into the drive assembly, and embodies one inventive solution, as described below. If driveshaft adaptor 60 is in its most proximal (to the left as illustrated) position, and/or piston assembly 10 is in its most distal position, then pin 64 may not be able to become engaged with groove 16, even when the cartridge is fully inserted so that notch 44 can be engaged by retainer 84, unless the components are configured, according to the invention, such that certain relative dimensions of the cartridge and driveshaft adaptor are provided, according to the invention, as described below.

FIG. 3 presents one set of controlled dimensions according to certain embodiments of the invention. The front and back ends of the cartridge are shown, as well as proximal 61 and distal 63 positions of the driveshaft adaptor 60, the groove 16 and the piston 22. Distance (a) is the distance separating proximal engaging pin 64 and distal engaging pin 84 on the reusable pump drive assembly, when driveshaft adaptor is in its most distal position at the end of a discharge stroke. Distance (b) is the distance separating proximal engaging pin 64 and distal engaging pin 84 on the reusable pump drive assembly, when driveshaft adaptor is in its most proximal position at the start of a discharge stroke. Distances (a) and (b) should be selected so that they correspond to the distances between groove 16 and groove 44 of the pumping cartridge, when the piston is in the fully distal position and fully proximal positions, respectively, in the normal operating zone of cylinder 32. The distance (c), representing the difference between (a) and (b) should thus be about the same as the travel distance of the piston and of the driveshaft during a pump stroke. Accordingly, it may be advantageous for cartridges and drive assemblies to be constructed to a common standard of dimensions (a) and (b) so as to be more effectively usable together.

Referring now to FIG. 4, the distance (d) between pin 64 and the front edge 70 of the driveshaft adaptor 60 may be essentially the same as the distance between the groove 16 and the lip 19 of the piston assembly 10. Alternatively, the distance between the groove 16 and the lip 19 of the piston assembly 10 could be somewhat longer than distance (d), or the lip 19 may not be present at all, in some embodiments. In these or other embodiments, the distance (e) between the pin 64 and the back of the driveshaft cavity 68 may be essentially the same as the distance between the groove 16 and the proximal end of the knob 14 (or functional equivalent).

Taking into account the above-discussed dimensional relationships, it is possible to arrange the reusable drive assembly and pumping cartridge configurations to facilitate reliable insertion of a pumping cartridge into a drive assembly so that the piston groove is properly positioned to be engaged by pin 64, or functional equivalent, once the cartridge is inserted into the block 80 or equivalent and positioned so that retainer 84 or equivalent can be engaged. In a first method of assembly, the piston assembly 10 is initially positioned proximally of the operating zone 46, i.e., "parked" proximally of the operating region (see FIG. 1). In the design shown in FIG. 1, this is the proximal end 48 of cavity 34. This region can optionally be machined to have a flange relief zone 36, in which the flange 26 on piston 22 is not compressed. Then, the piston can be positioned in this zone during manufacture, sterilization, and/or shipping, so that the sterilized cartridge is delivered to a customer ready to be inserted into the drive assembly without further manipulation. When the piston is pre-positioned in this way, the act of pushing the pumping cartridge into the drive assembly until it stops tends to facilitate the correct positioning of the lip 19 or of the knob 18 to allow for the engagement of the driveshaft adaptor 60 and engagement of pin 64 into groove 16, thereby reversibly connecting the piston assembly with the driveshaft.

In an alternative embodiment, the initial position of the piston can be irrelevant if certain control features are added to the drive assembly. In this embodiment, the cartridge is first inserted into block 80 and, optionally, retainer 84 is engaged. Then the driveshaft adaptor 60 is moved to its extreme distal position, under manual or electronic control. With proper dimensioning, as discussed above, this can ensure that groove 16 is positioned so that it can be engaged by pin 64, thereby connecting the piston assembly to the driveshaft adaptor. As an option, proper connection could be detected, for example by sensing the depth to which pin 64 penetrates into chamber 62 when engagement is attempted. Such an embodiment could also be supplemented by adding a controlling element that would position the driveshaft adaptor 60 at its most forward (distal) position upon shutdown of the drive assembly, or at its startup. This embodiment is also compatible with a pre-parked piston assembly version of the pumping cartridge, discussed above.

Useful additional features can be provided in certain embodiments. One optional feature is the provision of means for selectively controlling which of a variety of pumping cartridge types can be used with a particular drive assembly. For example, a cartridge of a first type requiring a higher pressure than other types of cartridges might be configured to not fit into or otherwise be unusable in an older drive assembly that cannot drive a cartridge to the required pressure. In one embodiment, the selective control means could comprise projections attached to outlet element 30 (see FIG. 1), or to other elements remaining outside of the drive assembly, that would prevent full insertion of the cartridge into the block 80 unless the drive and/or block had a mating feature, into which the pins could slide. In another embodiment, the cartridge and the drive assembly could contain electronic elements so that one could read the other's configuration, and would send signals to the operator, or to a system controller in the console, indicating a mismatch, and optionally interrupting the starting process of the drive assembly.

In the exemplary embodiment described above, the engaging mechanism between the reusable pump drive assembly and the pumping cartridge piston has been described as a pair of pins 64. The pins slide into the groove 16 on opposite sides of the piston shaft, as if the pins were a miniature tuning fork. In certain embodiments, the dimensions (e) and (d) (see FIG. 4) are selected such that the high force applied to the piston shaft in the compression stroke can be absorbed by lip 19 and/or knob 14 so that the pins 64 are not subject to high shearing forces. In such embodiments, the pins may only need to be configured with sufficient strength to enable them to withstand and transmit to the piston shaft, the lower force needed to slide the piston proximally on the return stroke. However, any of a variety of other latching mechanisms could provide the same or equivalent effect. As noted above, mechanical equivalents comprise any means of placing an engaging member so that it intrudes into groove 16, so that the piston is pulled backward during the return stroke.

The engaging/latching mechanism for engaging the piston shaft does not need to be locatable/movable inside of cavity 62, but could also, or alternatively, be mounted on forward face 70 of driveshaft adaptor 60 to engage a groove or other feature of the piston shaft. For example, in an embodiment where a groove is provided just proximally of lip 19, the piston shaft could be engaged there by a suitably positioned engaging mechanism.

Another embodiment for achieving operable engagement between the piston shaft and cavity 62 of the drive adaptor 60 involves providing a configuration allowing the closing of (i.e reduction in diameter of) driveshaft cavity 62 upon piston shaft 18. For example, the driveshaft adaptor 60 could have a longitudinal cut through its cross-section extending distally through forward face 70 and could be squeezed shut by a collet, clamp, etc. Or, in another embodiment, a collet element could be rotated to induce grasping of piston shaft 18. In another alternative, the groove 16 in piston shaft 18 could be replaced by a slot or a hole in or through piston shaft 18. This alternative could require providing a means for controlling the rotational orientation of piston shaft 18 within cavity 60.

Removable/disposable pumping cartridge configurations that can be used, or can be modified, for example as described below, to be usable, in the context of the present invention are described in US 2002-0176788-A1, along with information regarding materials of construction of the various components and methods of fabrication. Many such cartridges are suitable for use in the pressure range of 20,000 p.s.i or more. For designs for use at such high operating pressures, operating with relatively short piston stroke lengths and at high reciprocation frequency can be advantageous. The following recites certain exemplary ranges of dimensions that may be advantageously employed in practicing certain embodiments of the invention in which pumping cartridges are intended to be operated at pressures in the 5,000-20,000+ p.s.i. pressure range. In such embodiments, piston shaft 20 may have a diameter of between about 7 to 13 mm. The stroke length (distance (c) in FIG. 3) may be in the range of between about 3 to 12 mm., depending both on the desired volume delivery rate and on drive speed. The shortest distance from notch 44 to groove 16, i.e., distance (a) in FIG. 3, may be in the range of between about 6 to 9 cm. When a "parking region" for the piston is present in the pumping cartridge cylinder, its length may be similar to the stroke length, but somewhat larger than the length of the piston 22, for example in the range of between about 5 to 15 mm.

As disclosed in US 2002-0176788-A1, in certain embodiments, at least some of the conventional roles of pistons and cylinders can be reversed, so that, for example, a piston can be held stationary while a cylinder assembly is moved back and forth. Likewise, a sealing element, analogous to flange 23 of piston 22 (see FIG. 3) may be positioned on a piston (as illustrated in FIG. 3), and/or on the wall of a cylinder. Such variations are considered to be included within the scope of the invention.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. In the claims (as well as in the specification above), all transitional phrases or phrases of inclusion, such as "comprising," "including," "carrying," "having," "containing," "composed of," "made of," "formed of," "involving," and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. In cases where the present specification and a document incorporated by reference include conflicting disclosure, the present specification shall control.

The invention claimed is:

1. A reusable pump drive system, the system comprising:
    a pump cartridge having a piston assembly and a cylinder assembly,
        the piston assembly comprising a connecting region and a body region, the connecting region of the piston assembly comprising a piston shaft, the body region of the piston assembly comprising a body having a side wall, a check valve,
        a fluid inlet extending from outside the cylinder assembly through the side wall of the body to the check valve for introducing a fluid into the pump cartridge,
        a piston having a sealing flange, and
        an annular groove in an outer surface of the cylinder assembly,
    a drive shaft adapter having an inner radial cavity to receive a portion of the piston shaft, a first end portion, a second end portion and one or more piston shaft retaining components,
    a fixed guide member having an inner radial passage extending therethrough, and
    a pump cartridge cylinder retaining component having a distal engagement pin with an inner end sized and positionable to engage the annular groove on the cylinder assembly,
    wherein in a first position the pump cartridge cylinder retaining component retains the cylinder assembly in the inner radial passage and in a second position the pump cartridge cylinder retaining component allows insertion of the cylinder assembly into the inner radial passage or removal of the cylinder assembly from the inner radial passage.

2. The reusable pump drive system of claim 1, wherein the one or more piston retaining components comprises one or more tubular members.

3. The reusable pump drive system of claim 2, wherein at least one of the one or more tubular members has a rounded terminal end.

4. The reusable pump drive system of claim 2, wherein the one or more piston retaining components includes a lifting member coupled thereto for selectively engaging the one or more tubular members with an annular groove of the piston shaft.

5. The reusable pump drive system of claim 1, wherein the piston shaft includes an annular groove.

6. The reusable pump drive system of claim 5, wherein the one or more piston shaft retaining components engages with the annular groove to allow the pump cartridge and the drive shaft adapter to cooperatively move in a reciprocating motion.

7. The reusable pump drive system of claim 1, wherein the connecting region further comprises:
    a terminal knob,
    a groove,
    a shoulder, and the shaft.

8. The reusable pump drive system of claim 1, wherein the cylinder assembly comprises:
    a wall surrounding a cavity.

9. The reusable pump drive system of claim 8, wherein the cavity includes a proximal portion forming a piston storage region to accommodate a flange of the piston.

10. The reusable pump drive system of claim 1, wherein the fluid inlet extends from a first end formed by a fluid inlet port at the side wall of the body to a second end formed by the check valve.

11. The reusable pump drive system of claim 1, wherein the fluid inlet is configured to introduce a high pressure fluid from outside the pump cartridge.

12. The reusable pump drive system of claim 1, wherein the pump cartridge is configured to operate at a fluid pressure of at least 5,000 pounds per square inch.

13. The reusable pump drive system of claim 1, wherein the cylinder assembly defines a cavity therein, the cavity comprising an operating region in which the piston reciprocates during a pumping state, and a separate storage region at a proximal end of the cavity in which the piston is positioned during an inactive state to enable coupling of the one or more piston shaft retaining components to the piston shaft.

14. The reusable pump drive system of claim 13, wherein the drive shaft adapter is operable to reciprocate the piston in the operating region of the cavity during the pumping state, and to position the piston in the storage region of the cavity during the inactive state.

15. The reusable pump drive system of claim 13, wherein an inner surface of the storage region of the cylinder assembly comprises a relief configured to accommodate the flange of the piston assembly.

16. The reusable pump drive system of claim 13, wherein positioning of the piston in the storage region of the cylinder assembly enables coupling of the one or more piston shaft retaining components to the piston shaft regardless of a position of the drive shaft adapter.

17. The reusable pump drive system of claim 1, wherein the sealing flange includes an erodible sealing flange.

18. A reusable pump drive system, the system comprising:
   a pump cartridge having a piston assembly and a cylinder assembly,
      the piston assembly comprising a connecting region and a body region, the connecting region of the piston assembly comprising a piston shaft, the body region of the piston assembly comprising a body having a side wall, a check valve,
      a fluid inlet extending from outside the cylinder assembly through the side wall of the body to the check valve for introducing a fluid into the pump cartridge,
      a piston having a sealing flange, and
      an annular groove in an outer surface of the cylinder assembly,
   a drive shaft adapter having an inner radial cavity to receive a portion of the piston shaft, a first end portion, a second end portion and one or more piston shaft retaining components,
   a fixed guide member having an inner radial passage extending therethrough, and
   a pump cartridge cylinder retaining component with an inner end sized and positionable to engage the annular groove on the cylinder assembly,
   wherein in a first position the pump cartridge cylinder retaining component retains the cylinder assembly in the inner radial passage and in a second position the pump cartridge cylinder retaining component allows insertion of the cylinder assembly into the inner radial passage or removal of the cylinder assembly from the inner radial passage, the pump cartridge cylinder retaining component axially reciprocates along its longitudinal axis between the first position and the second position.

* * * * *